US006706277B2

(12) United States Patent
Day et al.

(10) Patent No.: US 6,706,277 B2
(45) Date of Patent: Mar. 16, 2004

(54) CONFECTIONERY COMPOSITIONS

(75) Inventors: Trevor Neil Day, Windsor (GB);
Donald James White, Jr., Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/146,270

(22) Filed: May 15, 2002

(65) Prior Publication Data
US 2003/0003219 A1 Jan. 2, 2003

Related U.S. Application Data

(60) Provisional application No. 60/291,176, filed on May 15, 2001.

(51) Int. Cl.$^7$ .................. A61K 7/16; A23G 3/00
(52) U.S. Cl. ................ 424/440; 426/660; 424/57; 424/435
(58) Field of Search .................. 424/48, 58, 95.1, 424/440; 426/3–6, 660

(56) References Cited

U.S. PATENT DOCUMENTS

| | | | |
|---|---|---|---|
| 3,678,154 A | * | 7/1972 | Widder et al. |
| 4,120,987 A | * | 10/1978 | Moore |
| 4,151,270 A | | 4/1979 | Ream et al. |
| 4,170,632 A | | 10/1979 | Wagenknecht et al. |
| 4,170,633 A | | 10/1979 | Wagenknecht et al. |
| 4,460,565 A | | 7/1984 | Weststrate et al. |
| 4,461,777 A | | 7/1984 | Murase et al. |
| 4,627,977 A | | 12/1986 | Gaffar et al. |
| 4,808,401 A | * | 2/1989 | Gaffar et al. |
| 4,908,211 A | | 3/1990 | Paz |
| 5,000,944 A | * | 3/1991 | Prencipe et al. |
| 5,017,385 A | * | 5/1991 | Wienecke |
| 5,094,844 A | | 3/1992 | Gaffar et al. |
| 5,306,519 A | * | 4/1994 | Peterson et al. |
| 5,618,518 A | | 4/1997 | Stookey |
| 5,702,687 A | * | 12/1997 | Miskewitz |
| 5,833,952 A | * | 11/1998 | Grigor et al. |
| 5,958,472 A | * | 9/1999 | Robinson et al. |
| 2002/0091846 A1 | * | 7/2002 | Lawlor |
| 2003/0003219 A1 | * | 1/2003 | Day et al. |
| 2003/0007937 A1 | * | 1/2003 | Lawlor |
| 2003/0007997 A1 | * | 1/2003 | Lawlor |
| 2003/0008062 A1 | * | 1/2003 | Day et al. |
| 2003/0049303 A1 | * | 3/2003 | Lawlor |

FOREIGN PATENT DOCUMENTS

| | | | |
|---|---|---|---|
| EP | 0007504 A1 | | 2/1980 |
| EP | 309 414 | * | 3/1989 |
| EP | 0309414 A2 | | 3/1989 |
| EP | 0333301 B1 | | 10/1993 |
| JP | 1215243 | | 8/1989 |
| JP | 8242771 | | 9/1996 |
| JP | 9295942 | | 11/1997 |
| JP | 10182388 | | 7/1998 |
| WO | 94/14407 | * | 7/1994 |
| WO | W0 99/12517 A 1 | | 3/1999 |
| WO | 99/17735 | * | 4/1999 |
| WO | W0 99/44436 A1 | | 9/1999 |
| WO | W0 00/13521 A1 | | 3/2000 |
| WO | W0 01/34107 A1 | | 5/2001 |
| WO | 01/34107 | * | 5/2001 |
| WO | W0 01/39606 A1 | | 6/2001 |
| WO | 2001039606 | * | 6/2001 |
| WO | 2001056389 | * | 8/2001 |
| WO | 2001056399 | * | 8/2001 |
| WO | 2002019834 | * | 3/2002 |
| WO | 2002051392 | * | 7/2002 |
| WO | 2002091847 | * | 11/2002 |
| WO | 2002091848 | * | 11/2002 |
| WO | 2002092027 | * | 11/2002 |
| WO | 2002092028 | * | 11/2002 |
| WO | 2002092037 | * | 11/2002 |
| WO | 2002092038 | * | 11/2002 |
| WO | 2003000065 | * | 1/2003 |

* cited by examiner

*Primary Examiner*—Shep K. Rose
(74) *Attorney, Agent, or Firm*—Emelyn DeLeon Hiland

(57) ABSTRACT

Disclosed are stable portable oral care confectionery compositions, which provide enhanced anti-calculus effects, optionally combined with additional oral care benefits. The present invention also relates to use of such compositions to provide improved surface conditioning effects and reduced metal astringency. The confectionery compositions comprise:

(i) greater than about 1% of a polyphosphate material having an average anion chain length of greater than or equal to 4;

(ii) less than about 10% water; and (iii) a suitable confectionery carrier material comprising less than about 2% elastomer by weight of the composition.

24 Claims, No Drawings

CONFECTIONERY COMPOSITIONS

CROSS REFERENCE

This application claims priority under Title 35, United States Code 119(e) from Provisional Application Ser. No. 60/291,176, filed May 15, 2001.

FIELD OF THE INVENTION

The present invention relates to confectionery compositions such as breath mints, low boiled candy, hard boiled candy, coated candy, lozenges, oral pasta, pressed mints, throat drops and the like, that comprise polyphosphate with an average anion chain length of greater than or equal to 4 and wherein the confectionery composition comprises less than 10%, by weight of the composition, water and less than 2%, by weight of the composition, elastomer. Preferably this invention relates to non-cariogenic or so called "sugar free" confectionery compositions. More particularly this invention relates to compositions that have anti-calculus and surface conditioning effects in the oral cavity. Compositions of the present invention are suitable for use by humans or animals.

BACKGROUND OF THE INVENTION

Dental plaque is the name given to a deposit of material that accumulates on the teeth and adjacent surfaces of the oral cavity. It is the product of microbial growth in the oral cavity, primarily derived from the food/sugar residues in the mouth. Mucoproteins, minerals and food deposits present in the saliva, and dead cells in the mouth, also contribute to the formation of plaque. The build up of plaque enhances the formation of calculus, a hard mineral material that deposits on teeth. Calculus is formed when calcium phosphate crystals, which become entangled in the plaque film, become sufficiently closely packed together to aggregate and become resistant to deformation. The build up of both plaque and calculus on the teeth leads to a general decline in oral health resulting in an increase in the rate of formation of dental caries, an increase in the prevalence of gum disease and can also contribute to the staining of teeth and the presence of malodour. If left untreated these conditions can lead to severe oral disease and deterioration of the gums and teeth.

Several anti-plaque and anti-calculus agents are known in the art. One such material is linear or cyclic dehydrated polyphosphate, which is known to be an effective calcium/magnesium ion suppressor, a sequestrant and/or chelating agent and an effective inhibitor of calculus formation. Well-known examples are the water soluble hexametaphosphates, tripolyphosphate and pyrophosphates and the like. These materials have been widely disclosed in oral care compositions such as dentifrice. Examples of such disclosures include U.S. Pat. No. 5,094,844 which discloses oral compositions comprising tripolyphosphate; U.S. Pat. No. 4,460,565 which discloses oral compositions comprising two or more fluoride compounds and an agent capable of supplying calcium ions to the teeth optionally in conjunction with a cyclic phosphate; WO 99/12517 which discloses oral compositions comprising tripolyphosphate, pyrophosphate and PVP; JP 10-182388 which discloses compositions comprising cyclic and linear condensed phosphoric acid and curry extract and JP 9-295942 which discloses an agent for preventing tooth decay comprising at least 1 meta phosphate. Such polyphosphates are also known to provide a buffering effect within oral compositions comprising zinc (U.S. Pat. No. 4,170,632 and U.S. Pat. No. 4,170,633 both to Wagenknecht). In addition, the pending patent application PCT/US00/30808 reports that long chain linear polyphosphates with an average anion chain length of greater than or equal to 4 provide novel surface conditioning benefits to the teeth and mucosa. This leads to an improved cleaning impression.

However, one of the commonly known issues with polyphosphates, especially long chain polyphosphates, is that they are rapidly hydrolysed and therefore their efficacy is reduced over time. Furthermore, when the polyphosphate is introduced into the oral cavity, salivary enzymes quickly hydrolyse the material, again leading to a reduction in desired efficacy. The prior art suggests that this can be prevented by use of the polyphosphate in combination with fluoride and polyvarboxylate (U.S. Pat. No. 4,627,977 and EP 333,301). However, this provides several formulation limitations, both regarding the type of polyphosphate that can be used and in controlling the relative ratio of the polyphosphate to other ingredients. As such there are several opportunities to further optimise the formulation of oral care products comprising polyphosphate to overcome these hydrolysis issues.

Furthermore, there is currently a movement in the oral care industry to encourage consumers to use dental hygiene products throughout the day and to brush their teeth more often. However, this is at best inconvenient and is often not possible. As such significant developmental effort has been focused towards developing oral care products in forms which are portable, which can be used several times a day, particularly after eating and which provide anti-plaque and anti-calculus benefits comparable to those obtained by regular brushing with dentifrice. It is hoped that such a product will improve the oral hygiene of consumers. In addition, such a product would make it easier to provide good oral hygiene to children and pets where it is not always easy to regularly brush the teeth.

Confectionery compositions which are popular with both children and adults alike and which are retained in the oral cavity for substantial periods of time during consumption, would seem to make an ideal product form for a portable oral care product. The art of the development and manufacture of a wide range of confectionery compositions is well known. However, the high sugar content of such confectionery compositions has been recognised as a contributory factor in poor dental health. Developments have been made to produce "sugar free", or non-cariogenic, confectionery which retain their organoleptic properties but which do not contribute to the formation of dental plaque. More recently research has turned to developing confectionery compositions, particularly "sugar free" confectionery compositions, particularly chewing gum compositions, which comprise one or more oral care agents. One such example is WO 99/44436, which discloses coated chewing gum compositions which comprise materials with known oral care benefits. However, although chewing gum products have several advantages, they also have several disadvantages in that the chewing of gum is considered unsightly by some consumers and is not acceptable in certain societies. In addition, the chewing gum product format is not ideal for administering to pets and children. As such there is a need for a confectionery oral care product form, or range of forms, which are acceptable in a wide range of societies but which maintain high degrees of oral care efficacy, particularly anti-plaque and anti-calculus efficacy.

The use of polyphosphate in confectionery compositions has been reported in the art. Examples include EP 309,414 which discloses chewing gum compositions comprising gum base and an anti-calculus active selected from polyphosphate, citrates and malates; U.S. Pat. No. 4,908,211 which discloses chewing gum comprising a sanguinarine and optionally a polypyrophosphate; U.S. Pat. No. 5,702,687 which discloses chewing gum compositions optionally comprising pyrophosphate or polyphosphate compositions; pending patent application PCT/US00/17177 which discloses chewing gum compositions comprising polyphosphate and U.S. Pat. No. 4,151,270 which discloses chewing gum compositions optionally comprising tripolyphosphate. Whilst the teaching of the prior art provide useful teachings as to the development of chewing gum compositions comprising short chain polyphosphates they do not teach how to develop a wide range of non chewing gum confectionery compositions comprising polyphosphate. Nor do they teach how to formulate such compositions with excellent anti-calculus benefits. Finally the prior art does not teach how to stabilise long chain polyphosphates in the formulation such that the anti-calculus benefits are retained over time.

Low levels of polyphosphates are also known in the confectionery art for their ability to stabilise whippable emulsion systems. Examples include U.S. Pat. No. 4,120,987 which discloses aerated confectionery comprising water soluble protein hydrosylates, starches and phosphate salts; EP 7504 which discloses a whippable composition comprising whey protein, wheat protein, gelatine and polyphosphates; JP 8-242771 which discloses confectionery compositions comprising whey protein and optionally sodium polyphosphate; U.S. Pat. No. 4,461,777 which discloses oil in water emulsions comprising oil, fat, proteins, emulsifier, amino acid, sugars and optionally sodium hexametaphosphate; U.S. Pat. No. 5,306,519 which discloses a flavoured syrup comprising a sweetener, water and a sequestrant which is optionally polyphosphate; WO 00/13521 which discloses chewable protein based pet toys comprising protein, water, flavour, plasticiser, nutrients and which optionally comprise polyphosphates;

U.S. Pat. No. 5618,518 which discloses pet chews soaked in sodium hexametaphosphate solution; and JP 9-4069342 which discloses Japanese style sweets comprising soybean beta amylase, emulsifier and polymerised phosphate. Although the prior art provides useful teachings as to how to use low levels of polyphosphate salts to stabilise emulsion systems it does not teach how to prepare a wide range of stable confectionery compositions with anti-calculus efficacy.

Surprisingly, it has now been found that, when a confectionery composition is prepared comprising greater than 1% of a polyphosphate material with an average anion chain length of greater than or equal to 4, less than 10% water and a carrier material which comprises less than 2% elastomer, a stable, portable oral care composition is obtained with beneficial anti-calculus efficacy comparable to frequent brushing. In addition it has been found that such confectionery compositions provide surface conditioning effects resulting in a remarkable cleaning impression and positive mouth feel characteristics both during and following use. This reinforces the anti-calculus consumer benefit. Furthermore, by formulating the product in a wide range of confectionery forms, consumer acceptable portable oral care, which is easily administered to adults, children and pets, has been developed.

While not wishing to be bound by theory it is believed that when a confectionery composition is formulated comprising greater than 1% polyphosphate material with an average anion chain length of greater than or equal to four, the composition has an enhanced anti-calculus benefit vs that of shorter chain length polyphosphates. Furthermore, by ensuring that the confectionery composition comprises less than 10% water the polyphosphate remains stably formulated during storage thus retaining its anti-calculus efficacy. Adding the polyphosphate as a dry material further enhances this effect. This is because, due to the low level of water in the composition, the dry material does not become solubilised and thus cannot hydrolyse. Furthermore it is believed that the longer chain polyphosphate is hydrolysed more slowly in the oral cavity. This also results in enhanced anti-calculus benefit. In addition the long chain polyphosphates modify the surface hydrophilic and hydrophobic properties of the mucosal and tooth surfaces, which result in the surface conditioning effect experienced by the user. It has also been surprisingly found that the polyphosphate can help to reduce the astringency of a metallic ion. Additionally, this reduction in astringency can occur without significantly reducing the efficacy of the polyphosphate.

It is an object of the present invention to provide portable oral care product, suitable for use by adults, children and pets, with excellent anti-calculus efficacy. It is a further object of the present invention to provide a confectionery composition that provides improved intra-oral cleaning impression and smooth tooth surface impression to reinforce the oral care benefit. It is another object of the present invention to provide confectionery compositions comprising polyphosphate material with an average anion chain length of greater than or equal to four, and/or orally active metallic ions with reduced astringency. These and other objects of the present invention will become readily apparent from the detailed description that follows.

SUMMARY OF THE INVENTION

According to a first aspect the present invention relates to a confectionery composition comprising:
  (i) greater than about 1% of a polyphosphate material wherein the polyphosphate has an average anion chain length of greater than or equal to 4;
  (ii) less than about 10% water; and
  (iii) a suitable confectionery carrier material wherein the confectionery carrier comprises less than about 2%, by weight of the composition, elastomer.

According to a second aspect the present invention relates to a method of providing surface conditioning effects to the oral cavity of a subject comprising administering to the subject a confectionery composition comprising:
  (i) greater than about 1% of a polyphosphate material wherein the polyphosphate has an average anion chain length of greater than or equal to 4;
  (ii) less than about 10% water;
  (iii) a suitable confectionery carrier material wherein the confectionery carrier comprises less than about 2%, by weight of the composition, elastomer; and
retaining said composition in the oral cavity for at least 5 seconds, preferably at least 10 seconds, more preferably at least 15 seconds and most preferably at least 30 seconds.

According to a third aspect the present invention relates to a method of reducing astringency of a confectionery composition containing an orally active metallic ion for administration to a subject's oral cavity and retention for at least 5 seconds, preferably at least 10 seconds, more preferably at least 15 seconds and most preferably at least 30 seconds, comprising including in said confectionery composition:
  (i) greater than about 1% of a polyphosphate material wherein the polyphosphate has an average anion chain length of greater than or equal to 4;

(ii) from about 0.001% to about 5%, by weight of the composition, of metal salt comprising the orally active metal cation;

(iii) less than about 10% water; and (iv) a suitable confectionery carrier material wherein the confectionery carrier comprises less than about 2%, by weight of the composition, elastomer.

DETAILED DESCRIPTION OF THE INVENTION

While the specification concludes with claims, which particularly point out and distinctly claim the invention, it is believed the present invention will be better understood from the following description.

All documents cited are, in relevant part, incorporated herein by reference; the citation of any document is not to be construed as an admission that it is prior art with respect to the present invention.

Herein, "comprising" means that other steps and other ingredients which do not affect the end result can be added. This term encompasses the terms "consisting of" and "consisting essentially of".

All percentages and ratios used herein are by weight of the total composition and all measurements made are at 25° C., unless otherwise designated.

The term "safe and effective amount" as used herein means an amount of a compound, component, or composition sufficient to significantly induce a positive benefit, but low enough to avoid serious side effects, i.e. to provide a reasonable benefit to risk ratio, within the scope of sound medical judgement.

The term "orally active" as used herein means a material that provides either a cosmetic, prophylactic or therapeutic benefit within the oral cavity.

The term "confectionery" as defined herein means a solid, gum-like, or glassy composition optionally having a liquid centre filling and/or optionally coated which comprises greater than about 25% sugar or sugar alcohol. Such compositions usually have a sweet taste. Examples of confectionery products include, but are not limited to, breath mints, low boiled candy, hard boiled candy, coated candy, lozenges, oral pasta, pressed mints, throat drops and the like. As defined herein the term confectionery does not comprise chewing gum.

The term "chewing gum" as defined herein means a confectionery composition which is suitable for chewing and which comprises 2% or greater, by weight of the composition, of elastomer. This is because without this level of elastomer the composition has properties, which are either unsuitable for chewing or unsuitable to remain substantive over time whilst being chewed.

The term "elastomer" as defined herein means a non-digestible polymeric material, or mixture of materials, such as the materials typically used in chewing gum compositions.

The term "crunchy" as defined herein means that the product has a texture such that has a firm and slightly gritty texture and which produces a slight cracking noise upon consumption. It is preferred that the compositions have a texture of granulated sugar.

The term "surface conditioning" as defined herein means creating a hydrophilic tooth surface immediately after treatment; and maintaining these effects for extended periods of time after use.

Active and other ingredients useful herein may be categorised or described herein by their cosmetic and/or therapeutic benefit or their postulated mode of action. However, it is to be understood that the active and other ingredients useful herein can in some instances provide more than one therapeutic and/or cosmetic benefit or operate via more than one mode of action. Therefore, classifications herein are made for the sake of convenience and are not intended to limit an ingredient to the particularly stated application or applications listed.

The elements of the compositions and methods of the present invention are described in more detail below.

Polyphosphate

Compositions of the present invention comprise greater than about 1%, preferably from about 1.5% to about 50%, more preferably from about 2% to about 15%, even more preferably from about 3% to about 12%, and most preferably from about 5% to about 10%, by weight, of polyphosphate salt.

Polyphosphate is a widely used term, which relates to phosphate anions which have been polymerised by dehydration to form a polymer of the phosphate anion. The polyphosphates can exist as linear or cyclic materials or mixtures thereof. It is preferred that the polyphosphates are linear materials comprising only low levels of cyclic materials. Polyphosphates are also characterised by the average anion chain length of the polymer anion. For the purposes of this invention the polyphosphates referred to are those with an average anion chain length of 4 or greater. It is preferred that the polyphosphates have an average anion chain length of from about 6 to about 40, preferably of from about 10 to about 30; more preferably of from about 14 to about 25 and even more preferably of from about 18 to about 25, and mixtures thereof. Furthermore polyphosphates exist as salts. It is preferred that the polyphosphate is an alkali metal salt, ammonium salt or mixtures thereof, preferably a sodium or potassium salt or mixtures thereof and more preferably a sodium salt.

Polyphosphates with an average anion chain length of greater than four usually occur as glassy materials. As defined herein a "glassy" material is one which is amorphous. Preferred in this invention are the linear "glassy" polyphosphates having the formula:

wherein X is sodium, potassium, or hydrogen and n averages greater than or equal to 6 or mixtures thereof. Such polyphosphates are manufactured by FMC Corporation and are commercially known as Sodaphos (n≈6), Hexaphos (n≈13), and Glass H (n≈21). Hexaphos and Glass H are preferred with Glass H being the most preferred polyphosphate. These polyphosphates may be used alone or in combination. A broad range of phosphates and their sources are described in Kirk & Othmer, *Encyclopedia of Chemical Technology*, Fourth Edition, Volume 18, Wiley-Interscience Publishers (1996).

Furthermore, it is preferred that at least 25%, preferably at least 50%, more preferably at least 60% and most preferably at least 75%, by weight of the polyphosphates, of the polyphosphate has a particulate form. If desired 100% of the polyphosphate material can be formed from particulates. It is preferred that the particulate polyphosphate form has a minimum particle size such that the particles are retained by a 0.1 mm mesh, preferably a 0.112 mm mesh, more preferably a 0.16 mm mesh, even more preferably a 0.18 mm mesh and most preferably a 0.2 mm mesh wherein the meshes are selected from the DIN 4188 mesh series. Furthermore the particulate polyphosphate preferably has a maximum particle size such that it passes through a 2 mm mesh, preferably a 1 mm mesh, more preferably an 0.8 mm mesh, even more preferably a 0.5 mm mesh and most preferably a 0.4 mm mesh, again wherein the meshes are selected from the DIN 4188 mesh series. The solubility of the particulate polyphosphate is preferably at least 1 g per 100 ml at 25° C., more preferably at least 5 g, even more preferably at least 8 g, further more preferably at least 10 g, and most preferably at least 15 g per 100 ml at 25° C. Thus the solid particulate should be "sparingly soluble", or preferably more soluble, as the term is defined as in the British Pharmacopoeia, 1999, Volume 1. Whilst there is no limit on the upper solubility of the polyphosphate it is preferred that it is not "very soluble" in water. Finally it is preferred that the polyphosphate particles have a hardness greater than 1, preferably greater than 2 on the Mohs hardness scale. The particle size, solubility and hardness properties confer a crunchy texture to the polyphosphate, and thus to the confectionery itself. These properties have been designed such that they provide a crunchy texture during the first few minutes of mastication but that the particles dissolves over time leaving a product with a non-gritty residue. This crunchy texture can be used to reinforce the oral care benefits to the consumer and also have limited mechanical cleaning benefits thus helping to reduce plaque levels. Different crunchy textures can be obtained by milling the polyphosphate to the desired particle size or by blending different commercial grades of polyphosphate to achieve the desired crunch. It is preferred the that crunchy sensation remains consumer noticeable for at least 1 minute 30 seconds, preferably for at least 2 minutes and more preferably for at least 2 minutes 30 seconds. However it is also preferred that the crunchy texture has disappeared by 5 minutes, preferably by 4 minutes so that the material does not abrade the dentin or so that the product does not have a gritty residue.

It may be desirable to have a sustained release of the polyphosphate agent from the confectionery composition. This may be accomplished by incorporating into the composition a further polyphosphate material, particularly a divalent cationic salt such as a calcium salt, which has a lower aqueous solubility than the major polyphosphate material. This can be used to tailor the release rate of polyphosphate to a required profile. By weight percent, the polyphosphate of lower solubility is generally present in no more than half, preferably no more than a quarter of the level of the more soluble material. For example, the cationic material lower solubility polyphosphate is typically present in an amount of up to about 10%, preferably from about 0.05% to about 5%, and more preferably from about 0.1% to about 3%, by weight of the composition.

Polyphosphates such as those described not only have an anti-calculus benefit but they also provide surface conditioning effects to the teeth and other surfaces of the oral cavity. The surface conditioning effects include the effective desorption of portions of undesirable pellicle proteins; creating a hydrophilic tooth surface immediately after treatment; and maintaining these effects for extended periods of time after use. These effects result in a clean feeling, which lasts beyond consumption of the confectionery product itself and further contributes to the consumer experience.

The surface conditioning effects on a subject's teeth and oral mucosa can be measured in vivo. These measurements include consumer responses on questions concerning clean teeth and smooth teeth. The effect of creating a hydrophilic surface can be measured in terms of a relative decrease in water contact angles on air dried tooth and mucosal surfaces according to a method disclosed by Baeir et al "Biophysical Modeling of Acquired Pellicle Formation on Substrata of Varying Surface Energies—an in vivo study", *Caries Research,* 1984, 18:408–415. The overall surface conditioning effect can also be measured by quantitative consumer studies. The surface measurements are recorded in triplicate on two separate teeth and on two separate positions on the gingival surfaces.

Water

Compositions of the present invention comprise less than about 10%, preferably less than about 8%, more preferably less than about 5%, even more preferably less than about 3%, and most preferably less than about 2%, by weight of the composition, water. The low levels of water are required in order to ensure that the long chain polyphosphates are not hydrolysed in the final composition.

Water used in the preparation of commercially suitable compositions should preferably be of low ion content and free of organic impurities. The amount of water in a composition should be considered to be not only that added as free water, but also water, which is introduced with other materials, such as with sorbitol, silica, surfactant solutions and/or colour solutions. Furthermore, the amount of water should be considered by weight of the final composition as a whole including coat and/or filling, where appropriate.

Confectionery Carrier Material

Compositions of the present invention are confectionery compositions wherein the carrier material comprises less than about 2%, by weight of the composition, elastomer. The exact ingredients for each product form will vary from product to product and the specific techniques will be known by one skilled in the art. However there are some general ingredients which are common to all product forms and these are discussed in more detail below. Preferred product forms are pressed tablets, low boiled candy, hard boiled candy which are readily formulated with less than about 10%, by weight of the composition, water.

Confectionery compositions of the present invention comprise a carrier material. The carrier materials vary depending on the type of confectionery used and would be well known to one skilled in the art. It is preferred that the carrier material for compositions of the present invention are not in the form of a whippable or aerated emulsion. Confectionery compositions of the present invention should also comprise less than about 10%, preferably less than about 8%, more preferably less than about 5% and most preferably less than about 3%, by weight of the composition, gum base wherein a gum base can comprise a mixture of one or more elastomers, resins and plasticisers. Compositions comprise less than about 2%, by weight of the composition, elastomer.

Hard and low boiled candy carrier, pressed tablets and the like usually comprise greater than about 70% bulk sweetener including suitable sugar and sugar syrups including cariogenic and non-cariogenic materials. Low boiled candies can also comprise butter to form toffee. Compositions of the present invention can also comprise low levels of gum arabic, gelatine, agar agar powder and the like.

Confectionery compositions of the present invention can preferably be centre filled. Such products preferably comprise from about 60% to about 95%, more preferably from about 75% to about 85% of an edible shell and from about 5% to about 40%, preferably from about 15% to bout 25%, by weight of the composition, of an edible filling. It is possible that centre filled confectionery composition can comprise an oral care active in the edible shell and or a different oral care active, or mixture of actives, in the edible filling. In addition the composition can comprise different flavouring agents in the shell and the filling.

The confectionery products of the present invention may also comprise a crunchy particle dispersed throughout the carrier material. This crunchy particle should have the properties of the particulate polyphosphate disclosed earlier.

Furthermore, the confectionery compositions of the present invention can also be coated. The outer coating may be hard or crunchy. Typically, the outer coating will essentially consist of sorbitol, maltitol, xylitol, isomalt, and other crystallisable polyols. Furthermore the coating will typically consist of several opaque layers, such that the confectionery core is not visible through the coating itself, which can optionally be covered with a further one or more transparent layers for aesthetic, textural and protective purposes. The outer coating may also contain small amounts of water and gum arabic. A polyol coating can be further coated with wax. The coating is applied in a conventional manner by successive applications of a coating solution, with drying in between each coat, as described in WO99/44436. As the coating dries it usually becomes opaque and is usually white, though other colorants may be added. A polyol coating can be further coated with wax. The coating can further comprise coloured flakes or speckles. If the composition comprises a coat it is possible that one or more of the oral care actives can be dispersed throughout the coat. This is especially preferred if one or more oral care active is incompatible in a single phase composition with another of the actives.

Balance of the Composition

Compositions of the present invention preferably comprise safe and effective levels of one or more additional components. Such materials are well known and are readily chosen by one skilled in the art based on the oral care, physical and aesthetic properties desired for the compositions being prepared. Examples of such materials include, but are not limited to fats, solvents, waxes, emulsifiers, softeners, bulking agents, cationic material, buffers, whitening agents, alkali metal bicarbonate salts, thickening materials, humectants, water, surfactants, titanium dioxide, flavouring agents, colouring agents, and mixtures thereof. Those ingredients most commonly used are described in more detail below.

Oral Care Active

Compositions of the present invention preferably comprise from about 0.01% to about 50%, preferably from about 0.01% to about 20%, more preferably from about 0.01% to about 10%, by weight, of a further oral care active selected from anti-calculus agents, anti-plaque agents, fluoride ion sources, anti-microbial agents, oral malodour control agents, desensitising agents, H-2 antagonists, antioxidants, teeth colour modifying substances nutrients, and mixtures thereof. The oral care actives preferably contain an active at a level where upon directed use, the benefit sought by the wearer is promoted without detriment to the oral surface to which it is applied.

Oral care compositions or substances of the present invention may include many of the actives previously discussed in the art. The following is a non-limiting list of oral care actives that may be used in the present invention. It is not intended that the actives listed in these groups are mutually exclusive and a single active may be included in compositions of the present invention to have several effects.

Orally Active Metal Cation:

Compositions of the present invention optionally comprise an orally active metal cation. The metal cation can be any monovalent or divalent cation selected from the group consisting of zinc, manganese, copper, iron, cobalt, silver, selenium, tin and vanadium; preferably from the group consisting of zinc, manganese, copper, iron, silver, and tin; more preferably from the group consisting of zinc, copper, silver and tin and most preferably from the group consisting of zinc and tin.

A wide variety of salts are useful in the present invention. These include so called "water-insoluble salts" which have a solubility of less than about 0.5 g per 100 ml at 25° C. and "water soluble salts" which have a solubility of greater than or equal to about 0.5 g per 100 ml at 25° C. It is also possible to use mixtures of these salts. Such mixtures can have several advantages in the compositions of the present invention since they are likely to have different complexing properties with the polyphosphate anions. In addition they have different release rates in the saliva and can therefore act to provide controlled release profiles.

Examples of salts that are suitable for use herein include acetate, ammonium sulphate, bromide, chloride, chromate, citrate, dithionate, fluorosilicate, tartrate, fluoride, formate, iodide, nitrate, phenol sulphate, salicyclate, sulphate, gluconate, succinate, glycerophosphate, lactate and mixtures thereof; preferred are acetate, bromide, chloride, citrate, dithionate, tartrate, fluoride, formate, iodide, nitrate, sulphate, gluconate, succinate, lactate and mixtures thereof; and more preferred are acetate, chloride, citrate, sulphate, gluconate, succinate, lactate and mixtures thereof.

If stannous chloride is used it may be advantageous to premix the stannous chloride with sodium gluconate prior to incorporating the salt in the composition since this can help to stabilise the stannous ions.

When a metal cation is incorporated into compositions of the present invention, which additionally comprise polyphosphate, the additional benefit of reducing the astringency of the metal cations within the composition is obtained thus improving the taste. In order to maximise this benefit it is preferred that the molar ratio of polyphosphate anion to the total level of orally active metal cation should be in the range of from about 10:1 to about 1:1, preferably from about 5:1 to about 1:1, preferably from about 3:1 to about 1:1. As used herein the term "polyphosphate anion" refers to a single anion regardless of chain length. The level of polyphosphate anion should be calculated by assuming that all of the polyphosphate material has the chain length of the average anion chain length of the material as quoted by the manufacturer.

Compositions of the present invention preferably comprise from about 0.001% to about 5%, preferably from about 0.01% to about 2%, more preferably from about 0.1% to about 1% and most preferably from about 0.1% to about 0.5%, by weight of the composition, of metal salt comprising the orally active metal cation.

Anti-calculus Agents:

Anti-calculus agents known for use in dental care products include phosphate, pyrophosphate, polyphosphate (discussed above), phosphonate, polyphosphonate and mixtures thereof. Pyrophosphates are among the best known for use in dental care products. The pyrophosphate salts useful in the present compositions include the dialkali metal pyrophosphate salts, tetra-alkali metal pyrophosphate salts and mixtures thereof in their unhydrated as well as hydrated forms are the preferred species. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) and mixtures thereof. The pyrophosphate salts are described in more detail in Kirk and Othmer, *Encyclopeadia of Chemical Technology*, 3$^{rd}$ Edition, Volume 17, Wiley Interscience Publishers (1982). Additional anti-calculus agents include polyacrylates and other polycarboxylates such as those disclosed in U.S. Pat. No. 3,429,963 issued to Shedlovsky on Feb. 25, 1969 and U.S. Pat. No. 4,304,766 issued to Chang on Dec. 8, 1981; and U.S. Pat. No. 4,661,341 issued to Benedict and Sunberg on Apr. 28, 1987; polyepoxysuccinates such as those disclosed in U.S. Pat. No. 4,846,650 issued to Benedict, Bush and Sunberg on Jul. 11, 1989; ethylenediaminetetraacetic acid as disclosed in British Patent No. 490,384 date Feb. 15, 1937; nitrilotriacetic acid and related compounds as disclosed in U.S. Pat. No. 3,678,154 issued to Widder and Briner on Jul. 18, 1972; polyphosphonates as disclosed in U.S. Pat. No. 3,737,533 issued to Francis on Jun. 5, 1973; U.S. Pat. No. 3,988,443 issued to Ploger, Schmidt-Dunker and Gloxhuber on Oct. 26, 1976 and U.S. Pat. No. 4,877,603 issued to Degenhardt and Kozikowski on Oct. 31, 1989. Anticalculus phosphates include potassium and sodium pyrophosphates; sodium tripolyphosphate; diphosphonates such as ethane-1-hydroxy-1,1-diphosphonate, 1-azacycloheptane-1, 1-diphosphonate, and linear alkyl diphosphonates; linear carboxylic acids; and sodium zinc citrate and other soluble zinc salts.

Anti-Plaque Agents:

Anti-plaque agents are any substances which inhibit the accumulation of bacterial deposits on the surfaces of the oral cavity. Examples include xylitol and other anti-microbial agents.

Fluoride Ion Source:

Application of fluoride ions to dental enamel serves to protect teeth against decay. A wide variety of fluoride ion yielding materials can be employed as sources of soluble fluoride in the present compositions. Examples of suitable fluoride ion yielding materials are found in U.S. Pat. No. 3,535,421, Oct. 20, 1970 issued to Briner et al. and U.S. Pat. No. 3,678,154 Jul. 18, 1972 issued to Widder et al. Preferred fluoride ion sources for use herein include sodium fluoride, potassium fluoride, stannous fluoride, ammonium fluoride and mixtures thereof. Sodium fluoride is particularly preferred. Preferably the present composition provide from about 50 ppm to about 10,000 ppm, more preferably from about 100 ppm to about 3000 ppm of fluoride ions.

Anti Microbial Agents:

Antimicrobial agents can also be present in the oral care compositions or substances of the present invention. Such agents may include, but are not limited to, 5-chloro-2-(2,4-dichlorophenoxy)-phenol, commonly referred to as triclosan, and described in the Merck Index, 11$^{th}$ Edition, (1989), pp 1529 (entry no 9573) in U.S. Pat. No. 3,506,720, and in European Patent Application No. 0,251,591 of Beecham Group, Plc, published Jan. 7, 1988; phthalic acid and its salts including, but not limited to those disclosed in U.S. Pat. No. 4,994,262 published Feb. 19, 1991, preferably magnesium mono-potassium phthalate, chlorhexidine (Merck Index, no. 2090); alexidine (Merck Index, no. 222); hexetidine (Merck Index, no. 4624); sanguinarine (Merck Index, no. 8320); benzalkonium chloride (Merck Index, no. 1066); salicylanilide (Merck Index, no. 8299); domiphen bromide (Merck Index, no. 3411); cetylpyridinium chloride (CPC) (Merck Index, no. 2024); tetradecylpyridinium chloride (TPC); N-tetradecyl-4-ethylpyridinium chloride (TDEPC); octenifine; delmopinol; octapinol; and other piperidine derivatives; nicin preparations; zinc/stannous ion agents; antibiotics such as augmentin, amoxicilline, tetracycline, doxycycline, minocycline, and metronidazole; and analogues and salts of the above; methyl salicyclate; and mixtures of all of the above.

Oral Malodour Control Agents:

A wide variety of natural plant extracts have recently been shown to exhibit oral malodour control benefits. These extracts include extracts obtained from any part of the plant including the leaf, stem, bark, pulp, seed, flesh, juice, root and mixtures thereof. It is preferred that the extract is obtained from the leaf, pulp and seed, more preferably from the leaf or seed. Many different plants, or parts of plants, can be used to provide these extracts including tea, especially green tea, magnolia, gold thread, honeysuckle, grape, bergamot, grapefruit, orange, lemon, tangerine, mandarin, satsuma, clementine, lime, and mixtures thereof; preferably from green tea, magnolia, grape, grapefruit and mixtures thereof. Such extracts comprise a wide variety of biologically active materials. These include anthocyanins, flavanols, hydrolysable tannins, alkaloids, lipids, carbohydrates, simple sugars, protein and amino acids, alcohols, organic acids and mixtures thereof. Essential oils are also known to have anti-bacterial properties. These include thymol, geraniol, carvacrol, hinokitiol, eucalyptol, catechol (particularly 4-allyl catechol) and mixtures thereof. It is preferred that compositions of the present invention comprise from about 0.0001% to about 30%, preferably from about 0.001% to about 15%, more preferably from about 0.01% to about 10%, even more preferably from about 0.1% to about 5% and most preferably from about 0.25% to about 3%, by weight of the composition, of extract, essential oil and mixtures thereof.

Compositions of the present invention may optionally comprise zinc phytate in combination with natural extracts. The zinc phytate is believed to enhance the polyphenol breath protection efficacy and increase the stability of the polyphenol extract. Compositions of the present invention preferably comprise from about 0.1% to about 10%, more preferably from about 0.5% to about 5% and most preferably from about 1% to about 3%, by weight of the composition, of zinc phytate.

Another class of oral malodour control agents include absorbents. These are used to absorb, adsorb, bind or otherwise complex the volatile oral malodour materials. Examples of such agents include talc, mushroom extract, zeolite, cyclodextrin, silica shell and mixtures thereof. Such materials are preferably used at a level of from about 0.5% to about 10%, preferably from about 1% to about 5%, by weight of the composition.

Desensitising Agents:

Desensitising agents, or anti-pain agents, can also be present in the oral care compositions or substances of the present invention. Such agents may include, but are not limited to, strontium chloride, potassium nitrate, natural herbs such as gall nut, Asarum, Cubebin, Galanga, scutellaria, Liangmianzhen, Baizhi, etc. Analgesics, including low levels of non-steroidal anti-inflammatory agents, such as ketorolac, flurbinprofen, ibuprofen, naproxen, indomethacin, aspirin, ketoprofen, piroxicam and meclofenamic acid, may also be used as desensitising agents.

H-2 Antagonists: Histamine-2 (H-2) receptor antagonist compounds (H-2 antagonists) may be used in the oral care compositions of the present invention. As used herein, selective H-2 antagonists are compounds that block H-2 receptors, but do not have meaningful activity in blocking histamine -1 (H-1) receptors. Selective H-2 antagonists include those disclosed in U.S. Pat. Nos. 5,294,433 and 5,364,616 Singer et al., issued Mar. 15, 1994 and Nov. 15, 1994 respectively and assigned to Procter & Gamble, wherein the selective H-2 antagonist is selected from the group consisting of cimetidine, etintidine, ranitidine, ICIA-5165, tiotidine, ORF-17578, lupitidine, donetidine, famotidine, roxatidine, pifatidine, lamtidine, BL-6548, BMY-25271, zaltidine, nizatidine, mifentidine, BMY- 52368, SKF-94482, BL-6341A, ICI-162846, ramixotidine, Wy-45727, SR-58042, BMY-25405, loxtidine, DA-4634, bisfentidine, sufotidine, ebrotidine, HE-30-256, D-16637, FRG-8813, FRG-8701, impromidine, L-643728 and HB-408. Particularly preferred is cimetidine (SKF-92334), N-cyano-N'-methyl-N"-(2-(((5-methyl-1H-imidazol-4-yl)methyl)thio)ethyl)guanidine:

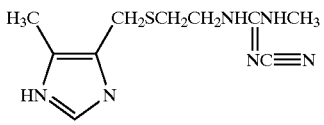

Cimetidine is also disclosed in the Merck Indes, 11$^{th}$ editions (1989), p354 (entry no 2279), and Physicians' Desk Reference, 46$^{th}$ edition (1992), p2228. Related preferred H-2 antagonists include burimamide and metiamide.

Antioxidants:

Antioxidants are generally recognised as useful in compositions such as those of the present invention. Antioxidants are disclosed in texts such as Cadenas and Packer, The Handbook of Antioxidants,® 1996 by Marel Dekker, Inc. Antioxidants that may be included in the oral care compositions of the present invention include, but are not limited to, Vitamin E, ascorbic acid, Uric acid, carotenoids, Vitamin A, flavenoids and polyphenols, herbal antioxidants, melatonin, aminoindoles, lipoic acids and mixtures thereof.

Teeth Colour Modifying Substances:

Teeth colour modifying substances may be considered among the oral care actives useful in the present invention. These substance are suitable for modifying the colour of the teeth to satisfy the consumer such as those listed in the CTFA Cosmetic Ingredient Handbook, 3$^{rd}$ Edition, Cosmetic and Fragrances Association Inc., Washington D.C. (1982), incorporated herein by reference. Specific examples include talc, mica, magnesium carbonate, calcium carbonate, magnesium silicate, aluminium magnesium carbonate, silica, titanium dioxide, zinc oxide, red iron oxide, brown iron oxide, yellow iron oxide, black iron oxide, ferric ammonium ferrocyanide, manganese violet, ultramarine, nylon powder, polyethylene powder, methacrylate powder, polystyrene powder, silk powder, crystalline cellulose, starch, titanated mica, iron oxide titanated mica, bismuth oxychloride, and mixtures thereof. Typical pigment levels from about 0.05% to about 20%, preferably from about 0.1% to about 15% and most preferably from about 0.25% to about 10%, by weight, of the composition.

Compositions for use herein may also comprise materials that remove or bleach intrinsic or extrinsic stains on or in tooth surfaces. Such substance are selected from the group consisting of the peroxides, metal chlorites, perborates, percarbonates, peroxyacids, persulphates, and combinations thereof. Suitable peroxide compounds include hydrogen peroxide, urea peroxide, calcium peroxide, carbamide peroxide and mixtures thereof. Suitable metal chlorites include calcium chlorite, barium chlorite, magnesium chlorite, lithium chlorite, sodium chlorite and potassium chlorite. Additional bleaching substances may be hypochlorite, and chlorine dioxide. A preferred percarbonate is sodium percarbonate. Preferred persulphates are oxones. The level of these substances is dependent on the available oxygen or chlorine. This level is generally used in compositions of the present invention at levels from about 0.1% to about 35%, preferably from about 1% to about 25% and most preferably from about 5% to about 10%, by weight of the composition.

Nutrients

Nutrients may improve the condition of the oral cavity and can be included in the oral care compositions or substances of the present invention. Nutrients include minerals, vitamins, oral nutritional supplements, enteral nutritional supplements, herbal supplements, natural extracts and mixtures thereof as disclosed in Drug Facts and Comparisons (loose leaf drug information service), Wolters Kluer Company, St Louis, Mo.,® 1997. Minerals that can be included with the compositions of the present invention include calcium, phosphorus, fluoride, zinc, manganese, potassium and mixtures thereof. Vitamins can be included with minerals or used separately. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Fish oil contains large amounts of Omega-3 (N-3) polyunsaturated fatty acids, eicosapentaenoic acid and docosahexaenoic acid.

Sweeteners

Two main types of sweeteners exist; bulk sweeteners and high intensity sweeteners. In general, the amount of sweetener used will vary depending on the sweetener and the overall desired aesthetics but levels used should be high enough such that the desired level of sweetness is achieved independent from the flavour. When bulk sweeteners are used they can also assume the role of the bulking agent or filler within the composition.

Bulk Cariogenic Sweetener:

Compositions of the present invention may comprise sweetener materials. Such materials include monosaccharides, disaccharides, polysaccharides and mixtures thereof. Examples include xylose, ribose, glucose, mannose, galactose, fructose, dextrose, sucrose, sugar maltose, fructo oligo saccharide syrups, partially hydrolysed starch, or corn syrup solids and mixtures thereof. However, such materials can often lead to the formation of cavities since they are readily metabolised by bacteria and other micro-organisms in the oral cavity. It is preferred that compositions of the present invention comprise less than about 10%, preferably less than about 5%, more preferably less than about 2%, even more preferably less than about 1%, and most preferably less than about 0.5%, by weight of the composition, of cariogenic sweetener. The composition can comprise 0% cariogenic sweetener if desired.

Bulk Non Cariogenic Sweeteners:

Compositions of the present invention preferably comprise a non-cariogenic sweetener. As used herein the term "non-cariogenic" refers to sweeteners which are not able to be metabolised by oral microbes and therefore do not contribute to the formation of dental caries. It is preferred that compositions of the present invention comprise greater than about 10%, preferably greater than about 20%, more preferably greater than about 30% and most preferably greater than about 40%, by weight of the composition, of non cariogenic sweetener. The composition can comprise up to 99% non-cariogenic sweetener if desired.

Preferred bulk non cariogenic sweetening agents are sugar alcohols such as sorbitol, xylitol, mannitol, maltitol, isomalt, hydrogenated starch hydrolisate, insulin, and other non-carigenic edible polyols such as glycerin and erythritol and mixtures thereof. Most preferred are non cariogenic sweeteners selected from the group consisting of maltitol, mannitol, xylitol, sorbitol, sucralose, aspartame and its salts, and mixtures thereof. In general compositions comprise from about 10% to about 80%, more preferably from about 30% to about 70%, by weight, of bulk sweetener.

High Intensity Sweeteners:

High intensity sweeteners are preferred over bulk sweeteners for use in compositions of the present invention because, for among other reasons, high intensity sweeteners may prolong the flavour of the finished gum composition during chewing. Suitable high intensity sweeteners include: dipeptide based sweeteners such as L-aspartyl-L-phenylalanine methyl ester (Aspartame) and equivalents (described in U.S. Pat. No. 3,492,131), L-α-aspartyl-N-(2, 2,4,4-tetramethyl-3-thietanyl)-D-alaninamide hydrate (Alitame) and the like; saccharin and its soluble salts eg sodium or calcium saccharin salts; cyclamate salts for example acesulfame-K and the like; chlorinated derivatives of sucrose such as chlorodeoxysucrose and the like; and protein based sweeteners, such as Thaumatin (talin). Compositions of the present invention preferably comprise from about 0.01% to about 2.0%, more preferably from about 0.05% to about 0.5%, by weight, of high intensity sweetener.

Bulking Agents

Bulking agents, such as fillers, can also be employed in confectionery. Suitable fillers and bulking agents are generally non-abrasive, preferably with an average particle size less than 5 μm, more preferably less than 3 μm and especially less than 1 μm. Illustrative bulking agents include calcium carbonate or ground limestone, talc, aluminium hydroxide, alumina, aluminium silicates, dicalcium phosphate and mixtures thereof. Compositions preferably comprise up to about 50%, more preferably up to about 30%, and most preferably up to about 10%, by weight, of bulking agent.

Flavouring Agents

Compositions of the present invention can preferably comprise a flavouring agent. As used herein the term "flavouring agent" means those flavour essences and equivalent synthetic materials which are added to flavour the composition. The flavouring agent can also include specific materials which are added to provide a warming or cooling sensation.

Flavouring agents are well known in the art. They include synthetic flavours and or oils and or essences derived from plants, roots, beans, nuts, leaves, flowers, fruits and so forth and mixtures thereof. Examples of suitable flavours include lemon, orange, banana, grape, lime, apricot, grapefruit, apple, strawberry, cherry, chocolate, pineapple, coffee, cocoa, cola, peanut, almond, liquorice, cinnamon and the like. The amount of flavouring agent employed is normally a matter of preference but in general they are used in amounts up to about 4%, preferably from about 0.1 to about 1%, by weight of the composition.

Compositions of the present invention can optionally comprise a cooling agent and suitable materials are described in WO 97/06695. Preferred for use herein are physiological cooling agents selected from the group consisting of menthol, peppermint oil, N-substituted-p-menthane-3-carboxamides, acyclic tertiary and secondary carboxamides, 3-1-methoxy propan-1,2-diol and mixtures thereof. Particularly preferred are menthol and menthol containing oils such as peppermint oil. Cooling agents are preferably used at a level of from about 0.001 to about 5%, more preferably from about 0.05% to about 3.5%, by weight of the composition.

Compositions of the present invention can optionally comprise a warming agent. Preferred agents include those selected from the group consisting of vanillyl alcohol n-butyl ether, vanillyl alcohol n-propyl ether, vanillyl alcohol isopropyl ether, vanillyl alcohol isobutyl ether, vanillyl alcohol n-amino ether, vanillyl alcohol isamyl ether, vanillyl alcohol n-hexyl ether, vanillyl alcohol methyl ether, vanillyl alcohol ethyl ether, ginerol, shogaol, paradol, zingerone, capsaicin, dihydrocapsaicin, nodihydrocapsaicin, homocapsaicin, homodihydrocapsaicin, ethanol, isopropyl alcohol, iso-amylalcohol, benzyl alcohol, chloroform, eugenol, cinnamon oil, cinnamic aldehyde, and mixtures thereof. Warming agents are preferably used at a level of from about 0.001 to about 5%, more preferably from about 0.05% to about 3.5%, by weight of the composition.

Preparation of Compositions

The compositions of the present invention are prepared by standard techniques well known to those skilled in the art. In order to prevent hydrolysis of the polyphosphate material it is preferred that the polyphosphate is not pre-dispersed in water prior to addition to the composition. It is therefore preferred that the polyphosphate be added as a solution. If the composition comprises more than one phase, in general the different phases will be prepared separately, with materials of similar phase partitioning being added in any order. The two phases will then be combined with vigorous stirring to form the multiphase system eg an emulsion or dispersion. Any ingredients in the formulation with high volatility, or which are susceptible to hydrolysis at high temperatures, will usually be added post mixing of the different phases with gentle stirring. Typical confectionery methods are highly suitable for manufacturing of compositions of the present invention. Finally if the products are coated the coating step is conducted as a final step. The coating can be applied by panning or spray dried techniques commonly known to those skilled in the art.

Method of Use

A second aspect of this invention relates to a method of providing surface conditioning effects to the oral cavity of a subject comprising administering to the subject a confectionery composition comprising:

(i) greater than about 1% of a polyphosphate material wherein the polyphosphate has an average anion chain length of greater than or equal to 4;

(ii) less than about 10% water;

(iii) a suitable confectionery carrier material wherein the confectionery carrier comprises less than about 2%, by weight of the composition, elastomer; and retaining said composition in the oral cavity for at least 5 seconds, preferably at least 10 seconds, more preferably at least 15 seconds and most preferably at least 30 seconds.

A third aspect of the invention relates to a method of reducing astringency of a confectionery composition containing an orally active metallic ion for administration to a subject's oral cavity and retention for at least 5 seconds, preferably at least 10 seconds, more preferably at least 15 seconds and most preferably at least 30 seconds, comprising including in said confectionery composition:

(i) greater than about 1% of a polyphosphate material wherein the polyphosphate has an average anion chain length of greater than or equal to 4;

(ii) from about 0.001% to about 5%, by weight of the composition, of metal salt comprising the orally active metal cation;

(iii) less than about 10% water; and (iv) a suitable confectionery carrier material wherein the confectionery carrier comprises less than about 2%, by weight of the composition, elastomer.

In order to maximise the effects of such methods it is preferred that the compositions of the present invention are formulated such that they remain in the oral cavity for at least 10 seconds. The methods are improved the longer the composition remains in the oral cavity. As such it is preferred that the compositions are formulated to encourage the consumer to retain them in the cavity. Such methods can be reapplied from 1 to about 10, preferably from 1 to about 5 and more preferably from 1 to about 3 times per day. It is preferred that such methods are used in combination with the usual oral hygiene routine of brushing the teeth at least once or preferably more often per day.

EXAMPLES

The following examples further illustrate the preferred embodiments within the scope of the present invention. These examples are given solely for the purpose of illustration and are not to be construed as limitations of the present invention as many variations of the invention are possible without departing from its spirit or scope. Unless otherwise indicated, all ingredients are expressed as a weight percentage of the composition.

Sugar is dissolved in water and heated under stirring to 110–112° C. Glucose syrup is then added and the mix heated to 141–142° C. to boil off water. Batch is drawn down under vacuum and polyphosphate/flavours added at approx 90° C. in low humidity environment. Batch is folded on a hot table and subsequently cooled on cold table (20° C.) prior to transfer to the batch forming and die cutting apparatus. Final product has a Glass like translucent appearance. Centre-filled candies are prepared by co-extruding liquid centre at same temperature as hard candy such that a liquid filled tube is formed which is passed through the die cutter to form sealed candies. Sugarfree candy making process is similar to above except the Isomalt is dissolved in water up to 110° C. and then cooked to 141–145° C. Rest of process is similar to sugarbased drops.

| | Hardboiled candy | | | | | | |
|---|---|---|---|---|---|---|---|
| INGREDIENT | I % w/w | II % w/w | III % w/w | IV % w/w | V % w/w | VI % w/w | VII % w/w |
| SHELL | | | | | | | |
| Sugar | 57.00 | 54.60 | 51.60 | — | — | 57.00 | — |
| Glucose syrup | 38.00 | 36.40 | 34.40 | — | — | 38.00 | — |
| Isomalt | — | — | — | 94.95 | 85.95 | — | 91.00 |
| Water | 3.00 | 3.00 | 3.00 | 3.00 | 3.00 | 3.00 | 3.00 |
| Sodium polyphosphate | 1.00 | 5.00 | 10.00 | 1.00 | 10.00 | 1.00 | 5.00 |
| Flavour | 1.00 | 1.00 | 1.00 | 1.00 | 1.00 | 1.00 | 1.00 |
| Acesulfam K | — | — | — | 0.05 | 0.05 | — | — |
| TOTAL | 100.00 | 100.00 | 100.00 | 100.00 | 100.00 | 100.00 | 100.00 |
| FILLING (20% w/w) | | | | | | | |
| High Fructose Corn syrup | — | — | — | — | — | 71.49 | — |
| Maltitol Syrup | — | — | — | — | — | — | 62.45 |
| Glycerin | — | — | — | — | — | 15.00 | 15.00 |
| Water | — | — | — | — | — | 12.00 | 12.00 |
| Sodium polyphosphate | — | — | — | — | — | 1.01 | 10.00 |
| Flavour | — | — | — | — | — | 0.50 | 0.50 |
| Acesulfam K | — | — | — | — | — | — | 0.05 |
| TOTAL | — | — | — | — | — | 100.00 | 100.00 |

| | Lowboiled candy | | | | | | | |
|---|---|---|---|---|---|---|---|---|
| INGREDIENT | VIII % w/w | IX % w/w | X % w/w | XI % w/w | XII % w/w | XIII % w/w | XIV % w/w | XV % w/w |
| Sugar | 43.32 | 41.12 | 38.37 | 39.43 | 45.52 | 41.72 | — | — |
| Glucose syrup | 39.58 | 37.78 | 35.53 | 42.47 | 32.38 | 34.18 | — | — |
| Isomalt | — | — | — | — | — | — | 75.85 | 75.85 |
| Xylitol | — | — | — | 5.00 | — | — | 5.00 | — |
| Water | 7.00 | 7.00 | 7.00 | 8.00 | 6.00 | 6.00 | 6.00 | 6.00 |
| Butter Fat | 5.00 | 5.00 | 5.00 | — | — | — | — | — |
| Sugared Condensed Milk | 3.00 | 3.00 | 3.00 | 3.00 | 3.00 | — | — | — |
| Vegetable Fat | — | — | — | — | 5.00 | 5.00 | 5.00 | 5.00 |
| Gelatine | — | — | — | — | 2.00 | 2.00 | 2.00 | 2.00 |
| Sodium polyphosphate | 1.00 | 5.00 | 10.00 | 1.00 | 5.00 | 10.00 | 5.00 | 10.00 |
| Flavour | 1.00 | 1.00 | 1.00 | 1.00 | 1.00 | 1.00 | 1.00 | 1.00 |
| Lecithin | 0.10 | 0.10 | 0.10 | 0.10 | 0.10 | 0.10 | 0.10 | 0.10 |
| Acesulfam K | — | — | — | — | — | — | 0.05 | 0.05 |
| TOTAL | 100.00 | 100.00 | 100.00 | 100.00 | 100.00 | 100.00 | 100.00 | 100.00 |

Sugar is slowly dissolved in water to 80° C. and subsequently rapidly heated to 105–108° C. when glucose syrup is added. The mixture is cooked to 118–130° C. at which point the heating is removed. Butter or other fat is added 2–3° C. lower than this final cook temperature. Gelatine, flavours, acid and polyphosphate are added after cooking has ended following which the final products are formed.

| | Compressed tablets | | | | |
|---|---|---|---|---|---|
| INGREDIENT | XVI % w/w | XVII % w/w | XVIII % w/w | XIX % w/w | XX % w/w |
| Compressable sugar | 96.70 | 87.20 | — | — | — |
| Dextrose | — | — | 95.95 | 86.90 | — |
| Sorbitol | — | — | — | — | 78.85 |
| Xylitol | — | — | — | — | 8.00 |
| Water | 0.50 | 1.00 | 0.50 | 1.00 | 1.00 |
| Gelatine | 0.30 | 0.30 | 0.30 | 0.30 | 0.30 |
| Sodium polyphosphate | 1.00 | 10.00 | 1.00 | 10.00 | 10.00 |
| Flavour | 1.00 | 1.00 | 1.00 | 1.00 | 1.00 |
| Gum arabic | — | — | 0.75 | — | — |
| Gum tragcanth | — | — | — | 0.30 | 0.30 |
| Magnesium Stearate | 0.50 | 0.50 | 0.50 | 0.50 | 0.50 |
| Acesulfam K | — | — | — | — | 0.05 |
| TOTAL | 100.00 | 100.00 | 100.00 | 100.00 | 100.00 |

A preformed solution of gelatine and gum products is prepared and sprayed over sugar or dextrose or isomalt to form a granular mixture. This is dried and sieved and subsequently compressed to form tablets.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A confectionery composition comprising:
   a) greater than about 1% of a water-soluble, surface-conditioning and anticalculus polyphosphate material having an average anion chain length of from about 6 to about 40;
   b) less than about 10% water; and
   c) a suitable confectionery carrier material comprising less than about 2% elastomer by weight of the composition, selected from hard boiled candy base, low boiled candy base, compressed sugar base and mixtures thereof,
   d) at least 25% of said polyphosphate being sparingly soluble particulates conferring a consumer noticeable crunchy texture which disappears within about 5 minutes of mastication without abrading dentin and leaving a gritty residue.

2. A composition according to claim 1 wherein the polyphosphate anion has an average anion chain length of from about 18 to about 25.

3. A composition according to claim 2, wherein the polyphosphate material is a glassy material.

4. A composition according to claim 1 wherein the polyphosphate is an alkali metal salt.

5. A composition according to claim 4 wherein the polyphosphate is a sodium or potassium salt.

6. A composition according to claim 1 wherein greater than about 25% by weight of the polyphosphate has a particle size such that it passes through a 2 mm mesh.

7. A composition according to claim 6 wherein greater than about 25% by weight of the polyphosphate has a particle size such that it passes though a 0.4 mm mesh.

8. A composition according to claim 1 wherein the polyphosphate has a particle size such that it is retained by a 0.1 mm mesh.

9. A composition according to claim 8 wherein the polyphosphate has a particle size such that it is retained by a 0.2 mm mesh.

10. A composition according to claim 1 wherein the polyphosphate material has an aqueous solubility of at least 1 g per 100 ml at 25° C.

11. A composition according to claim 10 wherein the polyphosphate material has an aqueous solubility of at least 15 g per 100 ml at 25° C.

12. A composition according to claim 11 wherein the polyphosphate material has a hardness of greater than 1 when measured using the Mohs hardness scale.

13. A composition according to claim 1 wherein the composition comprises from about 1.5% to about 50% by weight of polyphosphate salt.

14. A composition according to claim 13 if wherein the composition comprises from about 5% to about 10% by weight of polyphosphate salt.

15. A composition according to claim 1 wherein the composition comprises less than about 8% water by weight of the composition.

16. A composition according to claim 15 wherein the composition comprises less than about 2% water by weight of the composition.

17. A composition according to claim 1 wherein the composition comprises greater than about 10% of noncariogenic sweetener by weight of the composition.

18. A composition according to claim 17 wherein the composition comprises greater than about 40% of noncariogenic sweetener by weight of the composition.

19. A composition according to claim 17 wherein the non-cariogenic sweetener is selected from maltitol, mannitol, xylitol, sorbitol, sucralose, aspartame and its salts, and mixtures thereof.

20. A composition according to claim 1 wherein the confectionery composition has an outer coating.

21. A composition according to claim 1 wherein the composition further comprises from about 0.001% to about 5% of an orally active metallic ion by weight of the composition.

22. A method of providing surface conditioning effects to the oral cavity of a subject comprising administering to the subject a confectionery composition according to claim 1 and retaining said composition in the oral cavity for at least 5 seconds.

23. A confectionery composition containing an orally active metallic ion but having reduced astringency, said composition comprising:
   a) greater than about 1% of a water-soluble, surface-conditioning and anti-calculus polyphosphate material having an average anion chain length of from about 6 to about 40;
   b) from about 0.001% to about 5%, by weight of the composition, of metal salt comprising the orally active, astringency-conferring metal cation;

c) less than about 10% water; and
d) a suitable confectionery carrier material wherein the confectionery carrier comprises less than about 2% elastomer by weight of the composition and is selected from hard boiled candy base, low boiled candy base, compressed sugar base and mixtures thereof;
e) at least 25% of said polyphosphate being sparingly soluble particulates conferring a consumer noticeable crunchy texture which disappears within about 5 minutes of mastication without abrading dentin and leaving a gritty residue.

24. A method of reducing astringency of a confectionery composition containing an orally active metallic ion comprising administering a confectionery composition according to claim 23 to a subject's oral cavity and retaining said composition in the oral cavity for at least 5 seconds.

* * * * *